United States Patent [19]

Bezuglov et al.

[11] Patent Number: 5,625,083
[45] Date of Patent: Apr. 29, 1997

[54] DINITROGLYCEROL ESTERS OF UNSATURATED FATTY ACIDS AND PROSTAGLANDINS

[76] Inventors: Vladimir V. Bezuglov, Apt. 100, 9 Acad. Artsymovicha St., Moscow 117437; Igor V. Serkov, Apt. 119, 3 Institutskii Prospect, Chernogolovka Settlement, Moscow Province 152432, both of Russian Federation

[21] Appl. No.: 458,282

[22] Filed: Jun. 2, 1995

[51] Int. Cl.$^6$ .................................................. C07C 405/00
[52] U.S. Cl. .................................... 549/467; 560/121
[58] Field of Search ............................ 560/121; 549/467

[56] References Cited

FOREIGN PATENT DOCUMENTS 58-162556  9/1983  Japan .

Primary Examiner—Robert Gerstl

[57] ABSTRACT

The present invention relates to novel dinitroglycerol esters of fatty acids, hydroxy fatty acids and prostaglandins, and methods for producing them. Dinitroglycerol esters provided by this invention have an improved biological specificity and/or a greater specific activity than the parent compound. The novel prostanoids produced herein may be used as vasodilators, antihypertensive cardiovascular agents, bronchodilators, and they may have uses in obstetrics and gynecology. The dinitroglycerol esters of fatty acids and hydroxy fatty acids may be useful as platelet antiaggregating agents.

32 Claims, No Drawings

DINITROGLYCEROL ESTERS OF UNSATURATED FATTY ACIDS AND PROSTAGLANDINS

BACKGROUND OF THE INVENTION

The present invention relates to novel dinitroglycerol ester derivatives of unsaturated fatty acids, hydroxy unsaturated fatty acids, and eicosanoids, and to methods of making and using them. It provides dinitroglycerol esters of a wide variety of compounds such as polyunsaturated fatty acids, prostaglandins and hydroxy fatty acids, having useful and improved properties relative to the parent compounds. These improved properties include, but are not limited to: greater functional specificity, an enhanced ability to stimulate uterine contraction, an enhanced ability to modulate bronchial and arterial contractions, an enhanced ability to prevent platelet aggregation, and fewer side effects. The esters provided herein are more membrane-soluble than their precursor compounds, and can therefore more readily penetrate through membrane barriers.

Fatty acids and their oxygenated derivatives ("oxilipins") play an important role in the biochemical regulatory processes of a wide range of organisms, including humans. For example, fatty acids are essential structural and functional components of biological membranes. They are also key precursors of important bio-active metabolites such as prostaglandins, leukotrienes, hydroxy-polyenoic acids, etc. Many fatty acids have been shown to themselves possess important bio-regulatory properties (e.g., the ability to effect structural and functional changes in membranes and to alter the metabolism of target cells). Some derivatives of fatty acids possess a wide spectrum of biological activities. For example, it has been reported that anandamide (arachidonoylethanolamide) is a ligand for cannabinoid receptors (W. A. Devane et al., Science. Vol. 258, pp. 1946–1949, 1992), and arachidonoylamide was found to inhibit leukotriene biosynthesis (E. J. Corey et al. J. Am.. Chem. Soc., 1984, Vol. 106, p. 1503).

The term "oxilipin" denotes oxygenated compounds which are formed from polyunsaturated fatty acids by a reaction or reactions wherein at least one step is an enzymatically catalyzed oxygenation. Oxilipins include leukotrienes, eicosanoids such as prostaglandins and hydroxy- and epoxy- fatty acids with a chain length of 20 carbon atoms, as well as biosynthetically related compounds of longer (e.g., C22) and shorter (e.g., C18) chain length.

Prostaglandins ("PGs") are eicosanoid oxilipins synthesized by a wide variety of human tissues. They share in common a prostanoic acid skeleton described by the following formula:

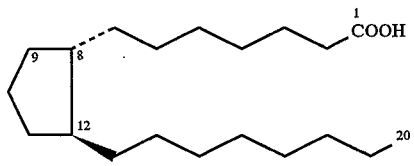

PGs are classified into several types according to the substituent groups present on their five-membered ring:

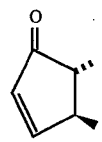 prostaglandins of A types

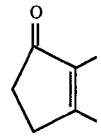 prostaglandins of B types

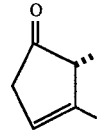 prostaglandins of C types

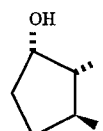 prostaglandins of D types

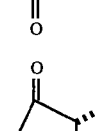 prostaglandins of E types

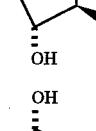 prostaglandins of F types

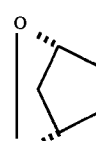 prostaglandins of H types

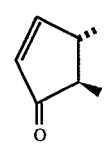 prostaglandins of J types

 prostaglandins of I types

They are also classified according to the placement of their double bonds

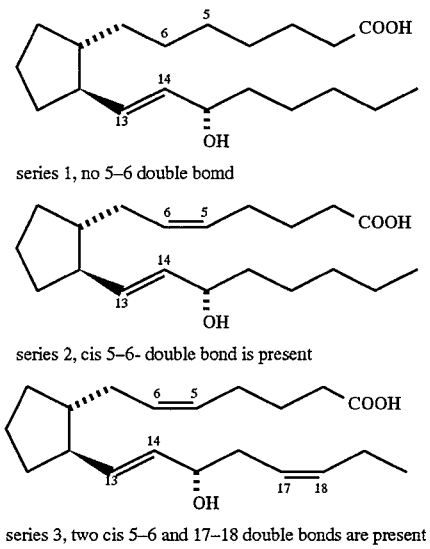

series 1, no 5-6 double bomd series 2, cis 5-6- double bond is present series 3, two cis 5-6 and 17-18 double bonds are present Prostaglandins have been shown to possess a wide spectrum of properties and to play an important role in a broad range of biological processes. These include, but are not limited to: hypertension, vasodilation, induction of inflammation and other immune responses, platelet aggregation, mediation of uterine and enteric muscle contraction, and ocular hypotension.

Despite their well-recognized potential for clinical utility in treating a variety of medical conditions, the medical uses of PGs and other fatty acid derived drugs have often been significantly limited by their metabolic and chemical instability and by the existence of undesirable side effects. There is therefore a great need to generate and test chemical derivatives of PGs having properties that are similar to or an improvement over those of the parent compound, while at the same time having fewer or less severe side effects.

A number of synthetic PG drugs have been produced and are presently at different stages of clinical study or already in medical use. See, e.g., Raduchel, B. and Vorbruggen, H., Prostaglandin Analogs, Advances in Prostaglandin, Thromboxane, and Leukotriene Research, Vol. 14, pp. 263–307 (1985) edited by J. Pike and D. R. Morton, Jr., Raven Press, N.Y. It is possible to generally divide these PG drags into two groups. The first group consists of PG analogs in which the natural structures have been radically altered. (e.g., ILOPROST—a stable $PGI_2$ analog, or ENPROSTIL—a $PGE_2$ analog in which sites of enzymic attack are protected chemically). These substances have relatively long half-lives. The other group includes natural PGs or PGs with localized ("dot") modifications (e.g., fluoroprostaglandins). In these instances the increase in the modified prostanoid's half-life is usually achieved by creating a drug form that enables the controlled release of prostaglandins.

Many pathologies of the cardiovascular system are related to, or accompanied by, an increased platelet aggregation. Well known examples are myocardial infarction, ischemic brain damage, thrombosis, shock, etc. The presently existing platelet anti-aggregation drugs have a comparatively low specific activity and anti-aggregation activity is only one of numerous side effects. There is a need for drugs combining a high anti-aggregation and vasodilating activities. Some of the novel fatty acid and prostaglandin derivatives described below have the potential to fill this gap.

SUMMARY OF THE INVENTION

It is an object of the present invention to provide chemically modified fatty acids, oxilipins, eicosanoids and related compounds useful in modulating and treating a variety of metabolic events and medical conditions. It is particularly a purpose of the invention to provide dinitroglycerol esters of fatty acids of the C18, C20, and C22 series, of their hydroxylated derivatives, and also of eicosanoids such as prostaglandins, a) having a greater metabolic and/or chemical stability than the parent compounds, b) that retain the desirable properties of the parent, or whose desirable properties are enhanced, c) but that exhibit reduced side effects. In addition, it is a primary objective of the present invention to provide novel compounds and pharmaceutical compositions for modulating or treating a variety of metabolic events and medical conditions, including uterine contraction, bronchial muscular pathologies, platelet aggregation and hypertension.

Accordingly, this invention provides a group of novel dinitroglycerol ester derivatives of fatty acids and of related compounds such as hydroxypolyenoic acids and prostanoids, and also methods for making them. The dinitroglycerol esters provided herein have improved properties as compared to the parent molecule. Preliminary data indicates that these new compounds, especially the prostanoid dinitroglycerol esters, are useful as vasodilators, peripheral cardiovascular agents, bronchodilators (mainly in acute cases), or for special purposes, such as protection of living body from noxious environmental factors. Some of these compounds have a pronounced ability to prevent human platelet aggregation. Early clinical studies indicate that a number of these compounds are suitable for use in clinical therapies.

The substances offered herein belong to a new class of fatty acids and oxilipin derivatives, combining in the same molecule two chemical moieties having distinct pharmacological activities. Our preliminary experiments indicate that a number of these "binary" compounds, e.g., the dinitroglycerol esters of prostaglandins, exhibit considerably higher specific activities and improved pharmacological properties as compared to the unmodified parent compounds.

DETAILED DESCRIPTION OF THE INVENTION

Our approach to drug engineering generally comprises combining in one molecule two chemically distinct pharmacophores: a lipid compound as, for example, a fatty acid or a fatty acid derivative such as a prostaglandin, and a second chemical moiety. By choosing carefully a bioactive compound for covalent attachment to the parent lipid moiety, it is possible to alter the pharmacological profile of the parent compound and to achieve a better tolerance of certain medical treatments.

Nitric oxide (NO) is a newly discovered biological mediator which acts as a transduction mechanism for the soluble guanylate cyclase or many cells, among them vascular smooth muscle. (See: S. Moncada, E. A. Higgs, J. R. Berrazueta "Clinical Relevance of Nitric Oxide in the Cardiovascular System", 1091, Edicomplet, S. A., Spain.) In the vasculature, NO mediates the actions of the so-called endothelium-derived relaxing factor (EDRF) and is a component of a powerful vasodilator mechanism that plays an important role in the physiological regulation of blood flow and pressure.

Nitrovasodilators, like nitroglycerin, act by imitating the actions of endogenous NO. Increasing evidence suggests that impaired production of NO may play a role in the origin of some conditions such as hypertension, platelet aggregation and atherosclerosis. These findings led us to choose NO-generating substances as the non-lipid component of the binary drug.

In the case of PGs, we generally utilized PGs or prostanoids with a "dot" modification of the natural structure. For example, in some cases, in order to protect PGs from degradation by 15-prostaglandin dehydrogenase, we used 15-fluorodeoxy prostaglandins as PG part of the binary molecule.

We decided against using PGs that have been extensively modified for several reasons. First, we wished to avoid working with PG preparations that might be degraded slowly and accumulate in sufficient quantities to cause harm in an organism. A permanently elevated level of PC-like material in the circulation is potentially dangerous, and could unbalance or disturb the regulatory system of the organism. Moreover, radically modified PGs are poor substrates for PG catabolizing enzymes and may be converted by the body into unknown toxic metabolites.

The majority of the substances discussed below were synthesized in 1–3 stages. The starting materials were either the natural fatty acids or PGs, or analogues having minor changes in the structure (e.g., prostanoids with a fluorine atom or with nitrogen bearing groups). This strategy enabled us to avoid stereochemical problems that might have caused problems in obtaining good yields of the desired products. In some cases the chemical modifications of PG structure were performed using methods that were developed by us. All reactions used gave satisfactory yields and could be easily adapted for large scale production.

The central reaction of this invention is the esterification of natural or modified PGs with glycerol dinitrate. The esterification was performed in three different ways: a) esterification through the corresponding intermediate aryl sulfonate; b) esterification through the corresponding intermediate imidazolide; and c) esterification through the corresponding intermediate acyl fluoride.

The first procedure (a) comprises the formation of a mixed anhydride of the starting compound and aryl sulfonic acid by reaction with an aryl sulfonylchloride (preferably p-toluene sulfonylchloride) in the presence of an organic base (preferably triethylamine) in an organic solvent such as toluene, benzene, dioxane, acetone, etc. The dinitroglycerol is added just after the addition of the aryl sulfonylchloride or after the complete formation of a mixed anhydride. A catalytic amount of 4-(dimethylamine)pyridine accelerates the reaction.

The second procedure (b) involves the formation of an intermediate imidazolide by reacting the starting compound with 1,1'-carbonyl- diimidazole in an organic solvent such as acetonitrile, tetrahydrofurane, nitromethane, etc. After completing of gas evolution a dinitroglycerol and acidic catalyst (preferable pyridinium hydrochloride) are added successively.

The third procedure (c) comprises the formation of an intermediate acyl fluoride by reacting the starting compound with a fluorinating agent (preferably morpholine trifluorosulfurane). The acyl fluoride can be purified or the next step may be performed without purification. The reaction of the acyl fluoride with dinitroglycerol proceeds smoothly in organic solvents such as benzene, dioxane, tetrahydrofurane, etc., in the presence of an organic base (preferable triethylamine).

The main products of the processes provided by this invention were dinitroglycerol esters of prostaglandins, having the following structural formula:

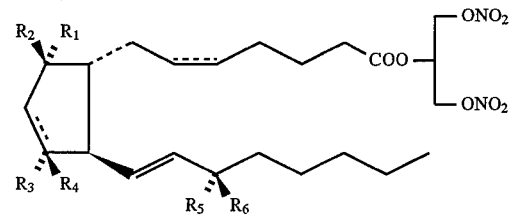

wherein one of the two groups bonded to the #9 carbon (either $R_1$ or $R_2$) is hydrogen and the remaining one ($R_2$ or $R_1$) is a hydroxyl, or alternatively, $R_1$ and $R_2$ together form an oxo group or a hydroxyimino group; and wherein one of the two groups bonded to the #11 carbon (either $R_3$ or $R_4$) is hydrogen and the remaining one ($R_4$ or $R_3$) is a hydroxyl, or alternatively, $R_3$ and $R_4$ together form an oxo group or a hydroxyimino group; with the condition that $R_3$ and $R_4$ do not form an oxo or hydroxyimino group when $R_1$ and $R_2$ for an oxo or hydroxyimino group; and wherein one of the two groups bonded to the #15 carbon (either $R_5$ or $R_6$) is hydrogen and the remaining one ($R_6$ or $R_5$) is a hydroxyl or fluorine: the symbol --- represents a single bond or a cis-double bound;

or dinitroglycerol esters of prostaglandins, having the following structural formula:

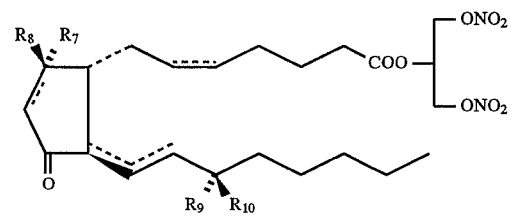

wherein $R_7$ or $R_8$ group bonded to the #9 carbon is a hydroxyl or hydrogen, the symbol --- represents a single bond or a double bound; with the conditions that $R_7$ or $R_8$ do not form a hydroxyl group when #10 and #11 carbons are bounded with double bond, or with the conditions that when $R_7$ or $R_8$ is a hydroxyl group #12 and #13 carbons are bounded with trans-double bond, and wherein one of the two groups at the #15 carbon (either $R_9$ or $R_{10}$) is a hydrogen atom and another group ($R_{10}$ or $R_9$) is a hydroxyl;

or dinitroglycerol esters of prostaglandins, having the following structural formula:

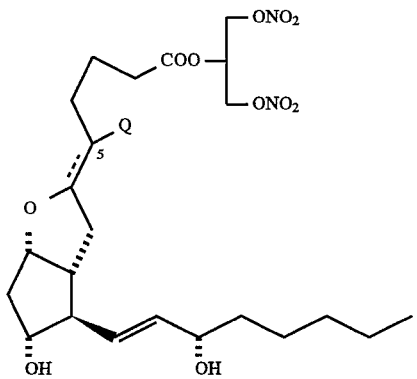

wherein Q group bounded to the #5 carbon is iodine or bromine, the symbol --- represents a single bond or a double bound; with the conditions that Q do not form a iodine or bromine group when #5 and #6 carbons are bonded with a double bond.

The reactions described above further yielded dinitroglycerol esters of fatty acids having the following structural formula:

wherein a=0–6, f=1–6, b=1–7 with the condition that the total carbon chain length is 18–22 atoms; and also dinitroglycerol esters of hydroxy fatty acids, having the following structural formula:

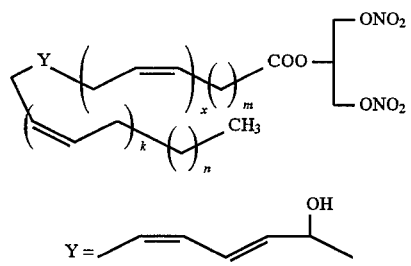

wherein m=1–7, x=0–4, k=0–4, n=0–3 with the condition that the total carbon chain length is 18–22 atoms.

All the starting materials were obtained either from the Experimental Plant of Organic Synthesis, Tallinn, Estonia (prostaglandins) or from the Pacific Institute of Fisheries and Oceanography (TINRO), Russia (fatty acids and hydroxy fatty acids). Prostaglandins $A_1$ and $A_2$ were prepared from corresponding prostaglandins $E_1$ and $E_2$ according to the procedure described in Corey E. J., et al., Total synthesis of pure dl-$E_1$, -$F_1$, -$A_1$, and -$B_1$ Hormones. J. Am. Chem. Soc., V. 90, pp. 3245–3247, 1968. 15-Fluoro- 15-deoxyprostaglandins were synthesized according to previously described procedures (see Bezuglov, V. V. and Bergelson L. D. (1979) The Synthesis of Fluoroprostaglandins. 11-Fluoro- and 15-fluoro prostaglandins. Bioorgan. Khim (Russian), v.5, pp. 1531–1536; Bezuglov V. V. et al., (1984) Synthesis of 15-fluorodeoxy Prostaglandins $A_2$ and $E_2$ from Prostaglandin $A_2$ Plexaura homomalla. Dokl. AN SSSR (Russian), v. 379, pp. 378–379; U.S. Pat. No. 4,665,214).

The novel dinitroglycerol esters disclosed herein can induce one or more of a multiplicity of biological events, rendering these compounds useful for a variety of pharmacological purposes. These biological events include platelet aggregation, modulation of smooth muscle stimulation, regulation of blood pressure, regulation of gastric secretion, NOSAC (=non-steroidal anti-inflammatory compound)-induced lesion inhibition, bronchodilation, nasal decongestion, peripheral vascular circulatory improvement, reproduction and fertility control, renal blood flow alteration, regulation of inflammation, and regulation of intraocular pressure.

Accordingly, the novel fatty acid, hydroxy fatty acids, and prostaglandin analogs of the present invention are used as agents in the study, prevention, control, and treatment of diseases and other undesirable physiological conditions, in mammals, particularly humans, valuable domestic animals, pets, zoological specimens, and laboratory animals (e.g., mice rats, rabbits and monkeys), as follows:

(a) Platelet Aggregation Inhibition

Some of the novel fatty acid, hydroxy fatty acid, and proslaglandin analogs provided herein can inhibit platelet aggregation, reduce the adhesive character of platelets, and potentially can remove or prevent the formation of thrombi in mammals, including man. These compounds can be used in the treatment and prevention of myocardial infarcts, to treat and prevent post-operative thrombosis, and to treat conditions such as atherosclerosis, arteriosclerosis, and blood clotting defects. They may also be useful in preparing platelet- rich concentrates for use in treating thrombocytopenia, chemotherapy, and radiation therapy. Other in vivo applications include treating geriatric patients to prevent cerebral ischemic attacks and long term prophylaxis following myocardial infarcts and strokes. For these purposes, these compounds are preferably administered systemically, e.g., intravenously, subcutaneously, intramuscularly, and in the form of sterile implants for prolonged action. Oral administration may be in the form of tablets, capsules, etc., administered 1 or more times daily. Doses can range from about 0.5 to 100 mg./kg. of body weight per day for rapid response, especially in emergency situations, the intravenous route of administration is preferred. Doses may range from about 0.01 to about 10 mg. per kg. of body weight per day; the exact dose depends on the age, weight, and condition of the patient or animal, and on the frequency and route of administration.

(b) Modulation of Smooth Muscle Contraction

Some of the novel fatty acid, hydroxy fatty acid, and prostaglandin analogs provided herein can modulate smooth muscle contraction, and may also potentiate other known smooth muscle stimulators (for example, oxalic agents, e.g., oxytocin, and the various ergot alkaloids including derivatives and analogs thereof). Therefore, they are useful in place of or in combination with reduced amounts of these known smooth muscle stimulators, for example, to control or prevent uterine bleeding after abortion or delivery, or to aid in expulsion of the placenta, and during the puerperium. For the latter purpose, the compound can be administered by intravenous infusion immediately after abortion or delivery. Subsequent doses can be given by intravenous, subcutaneous, or intramuscular injection or infusion during puerperium, the exact dose depending on the age, weight and condition of the patient or animal.

(c) Regulation of Blood Pressure

Some of the novel fatty acid, hydroxy fatty acid, and prostaglandin analog provided herein are useful as blood pressure regulators in mammals, including man. For this purpose, the compounds may be administered by intravenous infusion or in single or multiple doses. For the antithrombic application described above, these compounds are most preferably administered orally or by other convenient non-parenteral dosage form.

(d) Gastric Secretion Reduction

Some of these novel fatty acid, hydroxy fatty acid, and prostaglandin analogs may be useful in mammals, including man and certain useful animals, e.g., dogs and pigs, to reduce and control gastric secretion, thereby reducing or avoiding gastrointestinal ulcers, and accelerating the healing of such ulcers already present in the gastrointestinal tract. For this purpose, these compounds can be injected or infused intravenously, subcutaneously, or intramuscularly, or by injection or infusion, the exact dose defending on the age, weight, and condition of the patient or animal, and on the frequency and route of administration. Once healing of the ulcers has been accomplished, the maintenance dosage required to prevent recurrence is adjusted downward so long as the patient or animal remains asymptomatic.

(e) NOSAC-Induced Lesion Inhibition

The novel dinitroglycerol esters of this invention are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins. Some of the novel fatty acid, hydroxy fatty acid, and prostaglandin analog provided herein may be useful, for example, in reducing the undesirable gastrointestinal effects resulting from systemic administration of indomethacin, phenylbutazone, and aspirin.

The dosage regimen for the novel fatty acid, hydroxy fatty acids, and prostaglandin analog will depend upon a variety of factors, including the type, age, weight, sex and medical condition of the mammal, the nature and dosage regimen of the anti-inflammatory synthetase inhibitor being administered to the mammal, the sensitivity of the particular fatty acid, hydroxy fatty acids, and prostaglandin analog to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the novel fatty acid, hydroxy fatty acids, and prostaglandin analog to reduce and then substantially to eliminate those undesirable effects.

(f) Bronchodilation (Anti-asthma)

Some of the novel fatty acids, hydroxy fatty acids, and prostaglandin analogs are useful in the treatment of asthma. These compounds can control bronchospasms and facilitate breathing, and may be used to treat conditions such as bronchitis, bronchiectasis, pneumonia and emphysema. For these purposes, these compounds can be administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses can range from about 0.01 to 5 mg. per kg. of body weight, 1 to 4 times a day, the exact dose depending on the age, weight, and condition of the patient and on the frequency and route of administration. For the above use these fatty acid, hydroxy fatty acids, and prostaglandin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds can be effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as ethyl alcohol. Suitable means to employ the aerosol inhalation therapy technique are described fully in U.S. Pat. No. 2,868,691, for example.

(g) Nasal Decongestion

The novel fatty acid, hydroxy fatty acid, and prostaglandin analogs provided herein may be useful in mammals, including man, as nasal decongestants, administered in a pharmacologically suitable liquid vehicle or as an aerosol spray.

(h) Peripheral Vascular Circulatory Improvement

These compounds may be useful in treating peripheral vascular disease in humans and other mammals. The term peripheral vascular disease as used herein means disease of any of the blood vessels outside of the heart and disease of the lymph vessels, for example, frostbite, ischemic cerebrovascular disease, anheriovenous fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease.

(i) Reproduction and Fertility Control

The novel fatty acid, hydroxy fatty acid, and prostaglandin analogs provided herein, may be useful in place of oxytocin to induce labor in pregnant female animals, including man, cows, sheep, and pigs, at or near term, or in pregnant animals with intrauterine death of the fetus from about 20 weeks to term. For this purpose, the compound can be infused intravenously at a dose of 0.01 to 50 pg. per kg. of body weight per minute, until expulsion of the fetus.

These compounds may further be useful for controlling the reproductive cycle in menstruating female mammals, including humans. The compound may be administered systemically at a dose level in the range 0.01 mg. to about 20 mg. per kg. of body weight of the female mammal. Intravaginal and intrauterine routes are alternate methods of administration.

These compounds may further be useful in causing cervical dilation in pregnant and nonpregnant female mammals for purposes of gynecology and obstetrics. In cases of infertility, cervical dilation produced by these compounds may be useful in assisting sperm movement to the uterus. Cervical dilation by these compounds may also be useful in operative gynecology such as D and C (Cervical Dilation and Uterine Curettage) where mechanical dilation may cause perforation of the uterus, cervical tears, or infections.

It may also be useful for diagnostic procedures where dilation is necessary for tissue examination. For these purposes, these compounds may be administered locally or systemically.

These compounds are further useful in domestic animals (1) as an abortifacient, (2) as an aid to estrus detection, and (3) as regulators of the estrus. Domestic animals include horses, cattle, sheep, and swine. The regulation or synchronization of estrus allows for more efficient management of with conception and labor by enabling a herdsman to breed all female animals in short, pre-defined intervals. This synchronization results in a higher percentage of live births than the percentage achieved by natural control and, moreover, is especially important in facilitating artificial insemination (AI), by permitting a more economic insemination operation. These compounds may be injected or applied in a feed at doses of 0.1–100 mg per animal and may be combined with other agents such as steroids. Dosing schedules will depend on the species treated.

(i) Renal Blood Flow Alteration

The novel fatty acid, hydroxy fatty acid, and prostaglandin analogs provided herein may increase the flow of blood in the mammalian kidney, thereby increasing the volume and electrolyte content of the urine. For that reason, these compounds may be useful in managing cases of renal dysfunction, especially those involving blockage of the renal vascular bed. These compounds may be useful to alleviate and correct cases of edema resulting, for example, from massive surface burns, and in the management of shock.

(k) Dermatosis Treatment

These novel fatty acid, hydroxy fatty acids, and prostaglandin analogs may be useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness and noticeably, but incompletely cleared, or completely cleared.

For these purposes, these compounds can be applied topically as compositions including a suitable pharmaceutical carrier, for example as an ointment, lotion, paste, jelly, spray, or aerosol, using topical bases such as petrolatum, lanolin, polyethylene glycols, and alcohols. These compound, as the active ingredients, may constitute from about 0.1% to abut 15% by weight of the composition, preferably from about 0.5% to about 2%. In addition to topical administration, injection may be employed, as intradermally, intra- or peri-lesionally, or subcutaneously, using appropriate sterial saline compositions.

(l) Inflammation Reduction

The novel fatty acid, hydroxy fatty acids, and prostaglandin analogs provided herein may be useful as anti-inflammatory agents for inhibiting chronic inflammation in mammals including the swelling and other unpleasant effects thereof using methods of treatment and dosages generally described for the therapeutic agents in U.S. Pat. No. 3,885,041, which patent is incorporated herein by reference.

The novel fatty acid, hydroxy fatty acid, and prostaglandin analogs provided herein are thus surprisingly and unexpectedly useful for a wide variety of pharmacological purposes. Moreover, the fatty acid, hydroxy fatty acids, and prostaglandin analogs herein exhibit a more prolonged chemical stability, facilitating their formulation and use as pharmacological agents. Finally, these novel fatty acid, hydroxy fatty acids, and prostaglandin analogs exhibit improved utility as compared to fatty acid, hydroxy fatty acids, and prostaglandin when employed, as described above, as antithrombotic, antiasthma, or antiinflammatory agents. This improved utility is evidenced in that the novel fatly acid, hydroxy fatty acids, and prostaglandin analogs of this invention exhibit increased potency or selectivity of action, thus exhibiting fewer undesirable side effects when administered for one of these preferred pharmacological uses.

In determining the appropriate oral dosage and frequency of administration, a controlled dose titration is required. When used as the sole antihypertensive agent, determining the minimum effective dose required for adequate control of blood pressure is undertaken by initiating therapy at or near the threshold dose of patient or animal response. Thereafter upward adjustment of the dosage, until full control is achieved or undesired side effects are observed, is undertaken. In the event that systemic or side effects are observed, the dosage is lowered below the threshold at which such systemic or side effects are observed.

The preparations in the present invention are not construed to be limited to them, and suitable means for protection, oxidation, reduction and the like may be employed The dinitroglycerol esters of the present invention can be used as remedies for animal and human, and, in general, used for systemic or local application by oral administration, intravenous injection, subcutaneous injection, suppository, collyrium, oculentum and the like. The dosage varies depending on animals, human, age, weight, conditions, therapeutic effect, administration route, treatment time and the like.

The solid composition for oral administration of the present invention includes tablets, preparations, granules and the like. In such a solid composition, one or more active dinitroglycerol ester ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. The composition may also contain additives other than an inactive diluent, for example, a lubricant such as magnesium stearate; a disintegrant such as fibrous calcium gluconate: a stabilizer such as etherified cyclodextrin, for example, α, β- or γ-cyclodextrin, dimethyl-α; dimethyl-β-, trimethyl-β, or hydroxypropyl-β-cyclodextrin, branched cyclodextrin such as glucosyl-, maltosyl-cyclodextrin, formylated cyclodextrin, cyclodextrin containing sulfur, mitthoprotol, phospholipid and the like. When the above cyclodextrins are used, an inclusion compound with cyclodextrins may be sometimes formed to enhance stability. Alternatively, a phospholipid may be sometimes used to form a liposome, resulting in enhanced stability.

Tablets or pills may be coated with fine soluble materials in the stomach or intestine such as sugar, gelatin, hydroxypropyl cellulose, hydroxypropylmethylcellulose phthalate and the like, or with more than two layers. Further, they may be formed as capsules with absorbable substances such as gelatin.

A liquid composition for oral administration may contain a pharmaceutically acceptable emulsion, solution, suspension, syrup, elixir as well as generally used inactive diluent, for example, purified water, ethanol and the like. Such a composition may contain, in addition to the inactive diluent, adjuvants such as wetting agents and suspension, sweetening agents, flavoring agents, preseratives and the like.

Other compositions for oral administration include a spray formulated by known method, which may contain one or more active ingredients.

Injection for parenteral administration according to the present invention includes a sterile, aqueous or nonaqueous solution, suspension, emulsion and the like.

A diluent for such an aqueous solution and suspension includes, for example, injectable distilled water, physiological saline and ringer's solution.

A diluent for non-aqueous solution and suspension includes, for example, propylene glycol, polyethylene glycol, vegetable oil such as olive oil, alcohols such as ethanol, polysorbate and the like. Such a composition may contain adjuvants such as preservatives, wetting agents, emulsifiers, dispersants, stabilizers and the like. These are sterilized, for example, by filtration through a bacteria-holding filter, compounding with germicides, gas sterilization or radio-sterilization. These may be used by preparing a sterile solid composition and dissolving in sterile water or sterile solvent for injection before use.

EXAMPLES OF THE INVENTION

Example 1

1 g of prostaglandin $E_1$ was added under constant stirring to a mixture of 125 mls of toluene and 20 mls dry acetone. 1.46 g of triethylamine, 2 g of p-toluenesulfonyl chloride, 0.01–1 equivalents of 4-dimethyl- aminopyridine and and 1.5 g 1,3-dinitroglycerol were added, in this order, while the mixture was constantly stirred and maintained under an inert gas atmosphere. The complete mixture was stirred for 1 h at room temperature. The solid was then filtered through cotton wool and washed with 1 volume of toluene. The filtrate was concentrated in vacuo to ½ of the initial volume (approximately 70 mls). The concentrated filtrate was applied to the top of a 40×100 mm chromatography column packed with 120 mls of silica gel L (100–200 µm, CSFR) in benzene. The reaction products were eluted with a stepwise benzene—acetone gradient, starting with pure benzene, and followed by 10% (V:V) increments of acetone in benzene (e.g., 120 mls of 0% acetone in benzene, followed by 10% acetone in benzene, followed by 20% acetone in benzene, and so on up to 100% acetone). The fractions (20–30 mls were analysed by TLC and that contained the desired product were collected and evaporated in vacuo.

This procedure yielded the 1,3-dinitroglycerol ester of prostaglandin $E_1$: a viscous colorless oil, $R_f 0.51$ (benzene—dioxane-acetic acid, 20:10:1) NMR (CDCl$_3$), p.p.m.: 5.59 (2H, m), 5.38 (1H, m), 4.77, 4.57 (4H, 2dd), 4.09 (2H, m), 2.75 (2H, dd), 0.89 (3H, t), mass spectrum (FAB) m/z 517 (M+H), 501 (M+H—H$_2$O).

The following compounds were also prepared from the corresponding prostaglandins by the method described in the preceding paragraphs:

1,3-dinitroglycerol ester of prostaglandin $E_2$: a viscous colorless oil, $R_f 0.39$ (benzene-dioxane-acetic acid, 40:10:1); NMR (CDCl$_3$), p.p.m.: 5.6 (2H, m), 5.36 (3H, m), 4.74, 4.56 (4H, 2dd), 4.11 (2H, m), 2.72 (2H, dd), 0.92 (3H, t), mass spectrum (FAB) m/z 515 (M+H).

1,3-dinitroglycerol ester of prostaglandin $A_1$: a viscous colorless oil, UV $\lambda_{max}$ 218 nm, mass spectrum (FAB) m/z 501 (M+H), 483 (M+H–H$_2$O).

1,3-dinitroglycerol ester of prostaglandin $A_2$: a viscous yellow oil, UV $\lambda_{max}$ 218 nm, mass spectrum (FAB) m/z 499 (M+H), 481 (M+H–H$_2$O).

1,3-dinitroglycerol ester of prostaglandin $D_2$: a viscous colorless oil, mass spectrum (FAB) m/z 515 (M+H).

1,3-dinitroglycerol ester of prostaglandin $D_1$: a viscous colorless oil, mass spectrum (FAB) m/z 517 (M+H).

1,3-dinitroglycerol ester of 15-fluoro-15-deoxy prostaglandin $E_2$: a viscous colorless oil, $R_f 0.7$ (toluene-dioxane-acetic acid, 40:10:1), mass spectrum (EI), m/z 519, 498, 480, 472, 452, 371, 353, 316, 298.

1,3-dinitroglycerol ester of prostaglandin $F_{2\alpha}$: a viscous colorless oil, $R_f 0.25$ (benzene-dioxane-acetic acid: 20:10:1); NMR (CDCl$_3$), p.p.m.: 5.49 (2H, m), 5.34 (3H, m), 478, 458 (4H, 2dd), 4.14 (1H, m), 4.04 (1H, q), 3.9 (1H, m), 0.89 (3H, t), mass spectrum (FAB) m/z 517 (M+H), 501 (M+–H–H$_2$O).

1,3-dinitroglycerol ester of 11-epi-prostaglandin $F_{2\alpha}$: a viscous colorless oil, $R_f 0.25$ (benzene-dioxane-acetic acid; 20:10:1), mass spectrum (FAB) m/z 517 (M+H), 501 (M+H–H$_2$O).

1,3-dinitroglycerol ester of arachidonic acid: a viscous colorless oil, $R_f 0.37$ (benzene-hexane, 1:1).

1,3-dinitroglycerol ester of docosahexaenoic acid: a viscous colorless oil, $R_f 0.69$ (benzene).

1,3-dinitroglycerol ester of 9,12,15-octadecatrienoic acid: a viscous colorless oil, $R_f 0.61$ (benzene), mass spectrum (FAB) m/z 442 (M).

1,3-dinitroglycerol ester of 13-hydroxy-6,9,11-octadecatrienoic acid: a viscous colorless oil, $R_f 0.84$ (benzene-acetone, 4:1), mass spectrum (FAB) m/z 441 (M-H$_2$O+H).

Example 2

A solution of hydroxylamine hydrochloride (170 mg) and sodium acetate (215 kg) in 3 mls of 50% aqueous methanol were added under a nitrogen atmosphere to a stirred solution that contained 170 mg of 1,3-dinitroglycerol ester of prostaglandin $E_1$ in 1.5 mls of methanol. The reaction mixture was stirred at room temperature for 15 min, and then diluted with 5 mls of water. The methanol was evaporated in vacuo and the residue was allowed to crystallize. The resulting while crystalline powder was collected by filtering through a glass filter PO3, pore size: 15–30 micron (Universil, Hungary) and was dried under vacuum.

172 mg of 1,3-dinitroglycerol ester of 9-oxyiminoprostaglandin $E_1$ was obtained as a white crystalline powder, m.p. 81°–82° C., $R_f 0.55$ (chloroform-acetone, 1:1); NMR (CDCl$_3$), ppm.: 5.57 (2H, m), 5.39 (1H, m), 1.77, 4.67 (1H, 2 dd), 4.09 (1H, m), 3.87 (1H, m), 3.09 (2H, dd), 0.81 (3H, t), mass spectrum (FAB) m/z 534 (M+H).

By performing the analogous procedure using as starting materials the corresponding prostaglandins, the following compounds were also prepared:

1,3-dinitroglycerol ester of 9-oxyiminoprostaglandin $E_2$, a white crystalline powder, $R_f 0.54$ (chloroform-acetone, 1:1), mass spectrum (FAB) m/z 534 (M+H).

1,3-dinitroglycerol ester of 9-oxyiminoprostaglandin $A_2$, a white crystalline powder, $R_f 0.72$ (chloroform-acetone, 1:1).

1,3-dinitroglycerol ester of 9-oxyiminoprostaglandin $A_1$, a white crystalline powder, $R_f$ 0.72 (chloroform-acetone, 1:1).

Example 3

25 mg of sodium borohydride was added under a nitrogen atmosphere to a stirred solution of 24.8 mg of the 1,3-dinitroglycerol ester of prostaglandin $E_1$ in 2 mls of methanol at 0° C. The mixture was stirred for 20 min at 0° C. It then was diluted with 1 ml of water and 1 ml of saturated ammonium sulfate and extracted with ethyl acetate (2×5 mls). The combined organic extracts were washed with 2 mls water water, then with brine (a saturated sodium chloride solution), and dried over sodium sulfate. The dried organic solvent was evaporated to dryness in vacuo.

The residue was dissolved in MeOH and purified by HPLC (Column: SEPARON SGX (718 4.6×250 (Tessek, CSFR); detector UV 206 nm, sens. 0.32; Mobile phase: ACN- $H_2O$-AcOH 50:50:0.005, Flow rate: 1.2 ml/min; Temperature: 35° C.).

This procedure yielded 13.24 mg or the 1,3-dinitroglycerol ester of prostaglandin $F_{1\alpha}$: a viscous, colorless oil, $R_f$ 0.25 (benzene- dioxane-acetic acid, 20:10:1).

It also yielded 11.86 mg of the 1,3-dinitroglycerol ester of prostaglandin $F_{1\beta}$: a viscous, colorless oil, $R_f$ 0.16 benzene-dioxane-acetic acid, 20:10:1), mass spectrum (FAB) m/z 519 (M+H), 503 (M+H−$H_2O$).

The 1,3-dinitroglycerol ester of prostaglandin $F_{2\beta}$ was prepared by the same procedure from the corresponding ester of prostaglandin $E_2$: a viscous, colorless oil, $R_f$ 0.16 (benzene- dioxane-acetic acid, 20:10:1), mass spectrum (FAB) m/z 517 (M+H), 501 (M+H−$H_2O$).

Example 4

A solution of 100 mg of prostaglandin $A_2$ in 2 mls of methylene chloride was cooled under argon atmosphere to −78° C. 150 µl of morpholinetrifluorosulfurane were then added. The solution was mixed for 1 h at −78° C. 3 ml of saturated aqueous ammonium chloride solution were then added. The temperature of the reaction mixture was allowed to rise to room temperature. To the reaction mixture a 5 mls of water was added under vigorous mixing The organic layer was separated, and the aqueous layer was exhaustively extracted with chloroform (3×10 mls). The combined organic extracts were washed with water, brine, dried with sodium sulphate and vacuum-concentrated. The residue was dissolved in hexane and was applied to the top of a 5×100 mm chromatography column packed with 20 mls of silica gel L (40–100 mmk, CSFR) in hexane. The reaction products were eluted with a step gradient of hexane: diethyl ether, beginning with pure hexane, followed by successive 10% increments in the ether concentration (e.g., 20 mls of 0% ether in hexane, 10%, 20% and so forth to pure ether).

The final yield was 70 mg of 15-fluoro-15-deoxy prostaglandin $A_2$ fluoro anhydride: a viscous, yellow oil, $R_f$ 0.62 (benzene-ethyl acetate, 7:1), $\lambda_{max}$ 217 nm, mass spectrum (EI), m/z, 338 (M+), 318 (M—HF), 310 (M—CO), 298(m-2×HF).

70 mg of this 15-fluoro-15-deoxy prostaglandin $A_2$ fluoro anhydride was dissolved in 2 mls of benzene. 1,3-dinitroglycerol (75 mg), triethylamine (75 mg) and a catalytic amount (0.05–0.5 eqv.) of 4-dimethylaminopyridine was added under an inert gas atmosphere. The solution was mixed at 25° C. for 1 h. The mixture was then applied onto the top of a 15×100 mm chromatography column packed with 20 ml of silica gel L (40–100 µm, CSFR) in hexane. The reaction products were eluted with a gradient of hexane:diethyl ether, starting with pure hexane, followed by successive 10% increments of the ether concentration (e.g. 20 mls of 0%, 10%, 20% and so forth up to pure ether). Fractions containing the desired compound (analysed by TLC) were combined and evaporated in vacuo to yield 89.6 mg of pure 1,3-dinitroglycerol ester of 15-fluoro-15-deoxy prostaglandin $A_2$: a viscous, yellow oil, $R_{f 0.7}$ (benzene-ethyl acetate, 5:1), UV $\lambda_{max}$ 218 nm, mass spectrum (EI), m/z, 500 (M+), 480 (M—HF).

Example 5

100 mg of prostaglandin $E_2$ was dissolved in 2 mls of acetonitrile and 70 mg of carbonyldiimidazole (Fluka) was added under constant stirring. The reaction mixture was stirred 1.5 hours at room temperature (+21° C.) until the gas evolution entirely stopped. Then 0.1 mls of glycerol dinitrate and 70 mg of dry pyridinium hydrochloride were added, in this order, and the resulting mixture was stirred for 1.5–2 hours at room temperature and then diluted with 10 volumes of ethyl acetate and 2 volumes of water. The organic layer was washed first with a 2M solution of $NaHSO_4$, then with water (3×5 mls), then with brine. The organic layer was then dried over $Na_2SO_4$, filtered and evaporated in vacuo. The residue was dissolved in benzene and was then applied onto the top of a 15–100 mm chromatography column packed with 20 ml of silica gel L (40–100 µm, CSFR) in benzene. The reaction products were eluted with a step gradient of benzene and ethyl acetate, starting with pure benzene, followed by 10% (V/V) increments of ethyl acetate in benzene (e.g. 20 ml of 0%, then 10%, then 20% ethyl acetate in benzene, and so on, up to pure ethyl acetate). The fractions were analysed by TLC and that contained the desired compound were combined and evaporated in vacuo to yield 50 mg of pure 1,3-dinitroglycerol ester of prostaglandin $E_2$.

Example 6

By performing the procedure previously described (N. Fukushima, T. Kato, K. Ota, Y. Arai, S. Narumiya, O. Hayaishi. Biochem. Biophys. Res. Commun., 1982, Vol. 109, No 3, P. 626–633) using as starting material 1,3—dinitroglycerol esters of corresponding prostaglandins by their incubation in Tris-Cl buffer (0.05M, pH 7.2) at 30°–35° C., 1–3 days the following compounds were prepared:

1,3-dinitroglycerol ester of prostaglandin $J_2$, colorless oil, UV $\lambda_{max}$ 216 (EtOH);

1,3-dinitroglycerol ester of prostaglandin $J_1$, colorless oil, UV $\lambda_{max}$ 216 (EtOH).

Example 7

By performing the procedure previously described (G. L. Bundy, D. R. Norton, D. C. Peterson, E. E. Nishizawa, W. L. Miller. J. Med. Chem., 1983, Vol. 26, P. 790–799) using as starting material 1,3—dinitroglycerol esters of corresponding prostaglandins by action of 1,5-diazabicyclo[4.3.0]non-5-ene in tetrahydrofuran (room temperature, 12–18 hours) the following compounds were prepared:

1,3-dinitroglycerol ester of $\Delta^{12}$-prostaglandin $J_2$, yellowish oil, UV $\lambda_{max}$245 (EtOH);

1,3-dinitroglycerol ester of $\Delta^{12}$-prostaglandin $J_1$, yellowish oil, UV $\lambda_{max}$245 (EtOH);

1,3-dinitroglycerol ester of $\Delta^{12}$-prostaglandin $D_2$, colorless oil, UV $\lambda_{max}$244 (EtOH);

1,3-dinitroglycerol ester of $\Delta^{12}$-prostaglandin $D_1$, colorless oil, UV $\lambda_{max}$244 (EtOH).

Example 8

To the solution of 70 mg of 1,3-dinitroglycerol ester of prostaglandin $F_{2\alpha}$ in 2.5 mls of ether at +4° C. a saturated aqueous solution of sodium bicarbonate (6 mls) was added under constant magnet stirring and argon atmosphere followed by drop addition of iodine solution (145 mg) in ether (3.5 mls). The reaction mixture was stirred at +4° C. over night. The reaction mixture was diluted by 20 mls of ethers. The organic layer was separated, washed with aqueous 10% solution of $Na_2S_2O_3$, water, brine, dried over anhydrous sodium sulfate, filtered, and evaporated to dryness in vacuo. The residue was applied onto the top of a 15×80 mm chromatography column packed with 15 ml of silica gel L (40–100 μm, CSFR) in chloroform. The reaction products were eluted with a step gradient of chloroform and acetone, starting with pure chloroform, followed by 2% (V/V) increments of acetone in chloroform (e.g. 25 mls of 0%, then 2%, then 4% acetone in chloroform, and so on, up to 20% of acetone in chloroform). The fractions were analysed by TLC and that contained the desired compound were combined and evaporated in vacuo to yield 55 mg of pure 1,3-dinitroglycerol ester of 5-iodo-prostaglandin $I_1$: a viscous, colorless oil, $R_f$0.48 (chloroform-acetone, 1:2), mass spectrum (SIMS), m/z, 667 ($M^+$+Na), 627 ($M^+$—OH).

Example 9

The solution of 10 mg of 1,3-dinitroglycerol ester of 5-iodo-prostaglandin $I_1$ and 10 μl of 1,8-diazabicyclo[5.4.0]undec-7-ene in 2 mls of benzene was heated at reflux 2 hours. The reaction mixture was diluted by 6 mls of ether and washed rapidly with cold (+4° C.) water, and brine. The organic layer was filtered through 10 g of anhydrous sodium sulfate (in a glass funnel), and evaporated to dryness in vacuo to yield 8 mg of 1,3-dinitroglycerol ester of prostaglandin $I_2$ (prostacyclin); a viscous, slight yellowish oil, $R_f$0.45 (chloroform—acetone, 1:2), which was immediately dissolved in EtOH.

Example 10

To the solution of 100 mg of prostaglandin $E_2$ in 5 mls of dry, tetrahydrofuran 300 μl of hexamethyldisilazane and 150 μl of trimethylchlorosilane were added consistently under constant magnet stirring and argon atmosphere at room temperature for 2 hours. The reaction mixture was evaporated to dryness in vacuo. The residue was dissolved in 5 mls of dry benzene, and the resulting solvent was evaporated to dryness in vacuo. The final residue was dissolved in 0.5 mls of methylene chloride (solution a).

To the solution of 300 mg of morpholinetrifluorosulfurane in 4 mls of methylene chloride 200 μl of trimethylsilyl morpholine was added under constant magnet stirring and argon atmosphere at +4° C. and the reaction mixture was stirred for 1 hour at this temperature (solution b).

To the solution b the solution a was added by one portion under constant and vigorous magnet stirring and argon atmosphere at −65° C., and the resulting reaction mixture was stirred 30 min at −60°–40° C. To the cold reaction mixture 2 mls of brine was added and compounds were extracted with 5 volumes of ethyl acetate. The organic layer was separated, washed with water (3×5 mls), then with brine (1×5 mil). The organic layer was then dried over sodium sulfate, filtered and evaporated in vacuo.

The residue was dissolved in dry benzene, and 150 mg of 1,3-dinitroglycerol followed by 150 mg of triethylamine and 0.01–0.1 equivalents of 4-dimethylaminopyridine was added under constant magnet stirring at room temperature for 3 hours. The reaction mixture was evaporated in vacuo. The residue was dissolved in 2 mls of methanol and 100 μl of 1M aqueous hydrochloric acid was added. After 30 min the reaction mixture was diluted with 15 mls of ethyl acetate. The organic layer was separated, washed with water (3×5 mls), then with brine (1×5 mls). The organic layer was then dried over sodium sulfate, filtered and evaporated in vacuo. The residue was dissolved in benzene and was then applied onto the top of a 15×100 mm chromatography column packed with 20 mls of silica gel L (40–100 μm, CSFR) in benzene. The reaction products were eluted with a step gradient of benzene and ethyl acetate, starting with pure benzene, followed by 10% (V/V) increments of ethyl acetate in benzene (e.g. 20 mls of 0%, then 10%, then 20% ethyl acetate in benzene, and so on, up to pure ethyl acetate). The fractions were analysed by TLC and that contained the desired compound were combined and evaporated in vacuo to yield 50 mg of pure 1,3-dinitroglycerol ester of prostaglandin $E_2$.

A variety of biological experiments with some of the compounds made as described above demonstrated that they possess an increased pharmacological activity after esterification with glycerol dinitrate as compared to the parent compounds.

Example 11

TABLE 1

| Stability of ethanolic solution of NITROPROSTON. ||
| --- | --- |
| Time of storage, months | Relaxation of isolated rat aorta contracted with adrenaline, $ED_{50}$, $M*10^{-6}$ |
| 0 | 1.7 ± 0.15 |
| 1 | 1.54 ± 0.21 |
| 12 | 1.77 ± 0.148 |

Example 12

In experiments with rat and rabbit tissues, the hypertensive activity of dinitroglycerol ester of prostaglandin $E_2$ (NITROPROSTON) proved to be 5 times higher than that of the parent $PGE_2$. NITROPROSTON did not affect the heart rate in experimental animals, and no tachyphylaxis was observed. Another important feature of NITROPROSTON was its high vasodilating effect on the isolated rat aorta ($EC_{50}$ 0.68 mM), whereas PGE: induced muscle contraction in the same test.

These data suggest a potential use for NITROPROSTON in the treatment of cardiovascular diseases, especially of conditions accompanied by increased blood pressure and ischemia.

Another possible field of application of NITROPROSTON derives from its exceptionally high bronchodilating activity ($EC_{50}$ 7.18×10$^{-9}$M in isolated guinea pig trachea). A first series of experiments with volunteers and patients with bronchus obstruction has clearly demonstrated that NITROPROSTON given as a spray (5–7×10$^{-3}$ mg per dose) is a potent, effective bronchodilator. This raises the possibility of using NITROPROSTON to treat bronchospasms.

TABLE 2

PHARMACOLOGICAL ACTIVITY OF NITROPROSTON (DINITROGLYCEROL ESTER OF PROSTAGLANDIN $E_2$)

| PHARMACOLOGICAL TEST | ACTIVITY, $EC_{50}$, M$^{-6}$ | |
|---|---|---|
| | NITROPROSTON | $PGE_2$ |
| RAT BLOOD PRESSURE decrease ($ED_{20}$) | 2.7 ± 0.13 | 13.1 ± 0.2 |
| RAT UTERUS, contraction | 0.4 ± 0.1 | 0.08 ± 0.016 |
| ISOLATED RAT AORTA relaxation | 0.68 ± 0.12 | 84 ± 1 contraction |
| GUINEA PIG TRACHEA relaxation | 0.007 ± 0.025 | 0.14 ± 0.08 |
| RAT STOMACH contraction | 0.06 ± 0.01 | 0.04 ± 0.015 |

Example 13

NITROPROSTON protected laboratory animals from a variety of noxious factors. It increased the survival of mice in an atmosphere with elevated CO or $NO_2$ concentration: survival in the experimental group was 1.5–4 times higher than in the control group.

TABLE 3

INFLUENCE OF NITROPROSTON ON MICE SURVIVAL UNDER CONDITIONS OF HYPOBARIC HYPOXIA AND TOXIC CONCENTRATION OF CO OR $NO_2$

| Toxic factor | Survival, % | |
|---|---|---|
| | Control | Nitroproston, 1 mg/kg |
| Hypobary (9000 m) | 18.5 | 82 |
| CO (11 g/m$^3$) | 41 | 66 |
| $NO_2$ (700 mg/m$^3$) | 17 | 65 |

NITROPROSTON has a low toxicity (LD50 > 100 mg in mice).

Example 14

Pharmacological studies revealed that dinitroglycerol ester of prostaglandin $F_{2\alpha}$ (NITROPROST-F) was more than 10 times more effective than prostaglandin $F_{2\alpha}$ in stimulating rat uterine contractions ($EC_{50}$ 9×10$^{-9}$M and 110×10$^{-9}$M, respectively). At the same time, NITROPROST-F had a lower activity in rat stomach contraction and was as effective as prostaglandin $F_{2\alpha}$ on rat colon. These data suggest a potential for NITROPROST-F in the gynecology and obstetrics.

TABLE 4

PHARMACOLOGICAL ACTIVITY OF NITROPROST-F (DINITROGLYCEROL ESTER OF PROSTAGLANDIN $F_{2\alpha}$)

| PHARMACOLOGICAL TEST | ACTIVITY, $EC_{50}$, M$^{-6}$ | |
|---|---|---|
| | NITROPROST-F | $PGF_{2\alpha}$ |
| RAT UTERUS contraction | 0.009 ± 0.0017 | 0.11 ± 0.04 |
| ISOLATED RAT AORTA relaxation | 0.54 ± 0.19 | contraction |
| ISOLATED GUINEA PIG TRACHEA | 10 ± 1.5 relaxation | contraction |
| RAT STOMACH contraction | 0.13 ± 0.01 | 0.05 ± 0.015 |
| RAT COLON contraction | 0.175 ± 0.07 | 0.13 ± 0.071 |

Example 15

PROSTANIT (dinitroglycerol ester of prostaglandin $E_1$) is an active inhibitor of ADP-induced aggregation of human platelets ($IC_{50}$=0.19×10$^{-6}$M). In contrast to $PGE_1$, PROSTANIT displays a pronounced relaxing effect on the isolated rat aorta ($EC_{50}$=2.1×10$^{-6}$M). The combination of antiaggregatory and vasodilating properties suggests the possibility of using this drug in treatment of acute microcirculation disturbances.

The dinitroglycerol ester of 9-oxyiminoprostaglandin $E_1$ (NITROPROX) is characterized by a different combination of vasodilating ($EC_{50}$ 0.64 mM, rat aorta) and antiaggregating properties ($IC_{50}$ 1.1 mM, ADP- induced aggregation of human platelets).

Example 16

Improved antiaggregating properly showed also some dinitroglycerol esters of fatty acids, their mono-hydroxy derivatives and prostaglandins. For example, dinitroglycerol ester of arachidonic acid almost completely inhibited aggregation of human platelets induced by ADP (1×10$^{-5}$) in dose 0.1 mg/ml of plasma in spite of that the parent arachidonic acid is powerful inducer of platelet aggregation. Moderate antiaggregating activity (30–50% of inhibition of ADP induced human platelet aggregation) showed dinitroglycerol esters of octadecatrienoic, docosahexaenoic acid, and 5-hydroxyeicosapentaenoic acid. 1,3Dinitroglycerol ester of prostaglandin $D_2$ inhibited aggregation of human platelets induced by ADP (1×10M) in dose 0.1 mg/ml of plasma on 50%.

Example 17

TABLE 5
INFLUENCE OF NITRO-PGS SUBSTANCES ON LIPID SPECTRUM OF SERUM OF RATS WITH EXPERIMENTAL HYPERCHOLESTEROLAEMIA.

| Lipids or lipid fractions | Changes of the contents (%, relative to control) after therapy with: | | |
|---|---|---|---|
| | NITROPROSTON | NITROPROX | PROSTANIT |
| Total lipids Total serum | 67 | 92 | 72 |
| cholesterol (TSC) | 95 | 96 | 78 |
| Triglicerides | 95 | 79 | 72 |
| LDL cholesterol | 57 | 76 | 70 |
| HDL cholesterol (HDLC) | 123 | 114 | 76 |
| HDLC/TSC | 128 | 138 | 122 |

Lipids and lipid fractions in sera of rats with experimental hypercholesterolaemea were determined after one month of animal development with indicated drugs in a dose 15 µg/kg body weight intraperitoneally. 6 times per week. Rats not developed by drugs served as a control group.

Example 18

TABLE 6
INFLUENCE OF PROSTANOIDS ON PEROXIDATION OF SERUM OR TISSUE LIPIDS OF RATS WITH EXPERIMENTAL HYPERCHOLESTEROLAEMIA

| Prostaglandin | MDA level (%, relative to control) | | |
|---|---|---|---|
| | Serum | Liver | Aorta |
| Nitroproston | 85 | 77 | 44 |
| Nitroprox | 101 | 104 | 32 |

MDA contents as a parameter of lipid peroxidation were estimated after one month of animal development with indicated drugs in a dose 15 µg/kg body weight intraperitoneally, 6 times per week. Rats not developed by drugs served as a control.

We claim:

1. A dinitroglycerol ester of a prostaglandin of the formula:

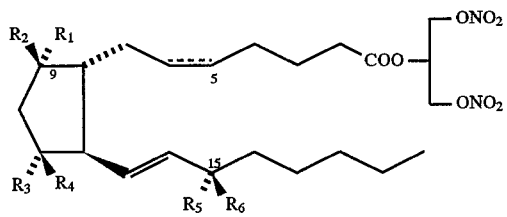

wherein one of $R_1$ and $R_2$ is hydrogen and the other is hydroxyl, or $R_1$ and $R_2$ taken together form an oxo group or a hydroxyimino group; one of $R_3$ and $R_4$ is hydrogen and the other is hydroxyl, or $R_3$ and $R_4$ taken together form an oxo group or a hydroxyimino group, provided that $R_3$ and $R_4$ do not form an oxo or hydroxyimino group when $R_1$ and $R_2$ form an oxo or hydroxyimino group; one of $R_5$ and $R_6$ is hydrogen and the other is hydroxyl or fluorine; and --- represents a single bond or a cis-double bond.

2. A compound according to claim 1, wherein $R_1$ and $R_2$ taken together form an oxo group; $R_3$ and $R_5$ are hydroxyl; $R_4$ and $R_6$ are hydrogen; and --- represents a single bond.

3. A compound according to claim 1, wherein $R_1$ and $R_2$ taken together form an oxo group; $R_3$ and $R_5$ are hydroxyl; $R_4$ and $R_6$ are hydrogen; and --- represents a cis-double bond.

4. A compound according to claim 1, wherein $R_1$ and $R_2$ taken together form an oxo group; $R_3$ is hydroxyl; $R_5$ is fluorine; $R_4$ and $R_6$ are hydrogen; and --- represents a cis-double bond.

5. A compound according to claim 1, wherein $R_1$ and $R_2$ taken together form an oxo group; $R_3$ is hydroxyl; $R_6$ is fluorine; $R_4$ and $R_5$ are hydrogen; and --- represents a cis-double bond.

6. A compound according to claim 1, wherein $R_1$ and $R_2$ taken together form an hydroxyimino group; $R_3$ and $R_5$ are hydroxyl; $R_4$ and $R_6$ are hydrogen; and --- represents a single bond.

7. A compound according to claim 1, wherein $R_1$ and $R_2$ taken together form an hydroxyimino group; $R_3$ and $R_5$ are hydroxyl; $R_4$ and $R_6$ are hydrogen; and --- represents a cis-double bond.

8. A compound according to claim 1, wherein $R_1$, $R_3$ and $R_5$ are hydroxyl; $R_2$, $R_4$ and $R_6$ are hydrogen; and --- represents a single bond.

9. A compound according to claim 1, wherein $R_2$, $R_3$ and $R_5$ are hydroxyl, and --- represents a single bond.

10. A compound according to claim 1, wherein $R_1$, $R_3$ and $R_5$ are hydroxyl; and --- represents a cis-double bond.

11. A compound according to claim 1, wherein $R_2$, $R_3$ and $R_5$ are hydroxyl; $R_1$, $R_4$ and $R_6$ are hydrogen; and --- represents a cis-double bond.

12. A compound according to claim 1, wherein $R_1$, $R_4$ and $R_5$ are hydroxyl; and --- represents a cis-double bond.

13. A compound according to claim 1, wherein $R_3$ and $R_4$ taken together form an oxo group; $R_1$ and $R_5$ are hydroxyl; $R_2$ and $R_6$ are hydrogen; and --- represents a single bond.

14. A compound according to claim 1, wherein $R_3$ and $R_4$ taken together form an oxo group; $R_1$ and $R_5$ are hydroxyl; $R_2$ and $R_6$ are hydrogen; and --- represents a cis-double bond.

15. A dinitroglycerol ester of a prostaglandin of the formula:

23

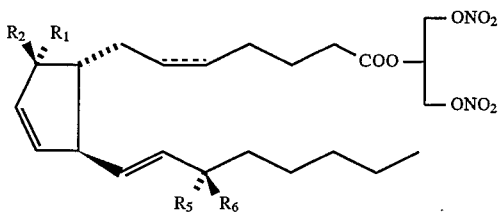

wherein $R_1$ and $R_2$ taken together form an oxo group or a hydroxyimino group; one of $R_5$ and $R_6$ is hydrogen and the other is hydroxyl or fluorine; and --- represents a single bond or a cis-double bond.

16. A compound according to claim 15, wherein $R_1$ and $R_2$ taken together form an oxo group; $R_5$ is hydroxyl; $R_6$ is hydrogen; and --- represents a single bond.

17. A compound according to claim 15, wherein $R_1$ and $R_2$ taken together form an oxo group; $R_5$ is hydroxyl; $R_6$ is hydrogen; and --- represents a cis-double bond.

18. A compound according to claim 15, wherein $R_1$ and $R_2$ taken together form an oxo group; $R_5$ is fluorine; $R_6$ is hydrogen; and --- represents a cis-double bond.

19. A compound according to claim 15, wherein $R_1$ and $R_2$ taken together form an oxo group; $R_6$ is fluorine; $R_5$ is hydrogen; and --- represents a cis-double bond.

20. A compound according to claim 15, wherein $R_1$ and $R_2$ taken together form a hydroximino group; $R_5$ is hydroxyl; $R_6$ is hydrogen; and --- represents a single bond.

21. A compound according to claim 15, wherein $R_1$ and $R_2$ taken together form a hydroxyimino group; $R_5$ is hydroxyl; $R_6$ is hydrogen; and --- represents a cis-double bond.

22. A dinitroglycerol ester of a prostaglandin of the formula:

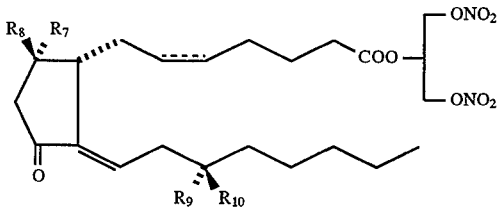

wherein $R_7$ and $R_8$ are each hydroxyl or hydrogen; one of $R_9$ and $R_{10}$ is hydrogen and the other is hydroxyl or fluorine; and --- represent a single bond or a cis-double bond.

23. A compound according to claim 22, wherein $R_7$ and $R_9$ are hydroxyl; $R_8$ and $R_{10}$ are hydrogen; and --- represents a cis-double bond.

24. A compound according to claim 22, wherein $R_7$ and $R_9$ are hydroxyl; $R_8$ and $R_9$ are hydrogen; and --- represents a single bond.

25. A dinitroglycerol ester of a prostaglandin of the formula:

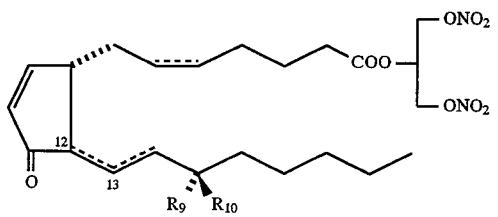

wherein one of $R_9$ and $R_{10}$ is hydrogen and the other is hydroxyl or fluorine; --- represents a single bond or a

24 double bond, and

represents two single bonds or an alternate single and double bond.

26. A compound according to claim 25, wherein $R_9$ is hydroxyl; $R_{10}$ is a hydrogen; --- represents a double bond; and

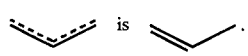

27. A compound according to claim 25, wherein $R_9$ is hydroxyl; $R_{10}$ is hydrogen; --- represents a single bond; and

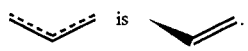

28. A compound according to claim 25, wherein $R_9$ is hydroxyl; $R_{10}$ is hydrogen; --- represents a single bond; and

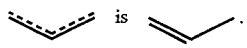

29. A compound according to claim 25, wherein $R_9$ is hydroxyl; $R_{10}$ is hydrogen; --- represents a double bond; and

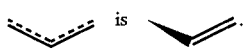

30. The dinitroglycerol ester of a prostaglandin of the formula:

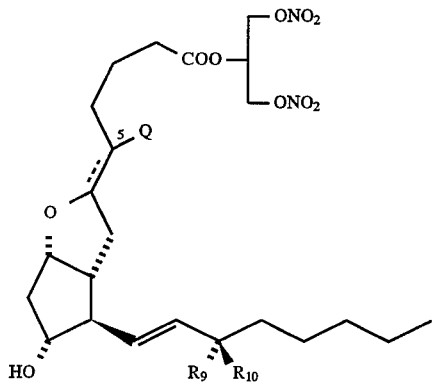

wherein Q is iodine or bromine when --- represents a single bond, and is hydrogen when represents a double bond; and one of $R_9$ and $R_{10}$ is hydrogen and the other is hydroxyl or fluorine.

31. A compound according to claim 30, wherein Q is iodine; and --- represents a single bond.

32. A compound according to claim 30, wherein Q is hydrogen; and --- represents a double bond.

* * * * *